United States Patent
Johnson (10) Patent No.: US 10,724,056 B2
(45) Date of Patent: *Jul. 28, 2020

(54) **METHOD OF PRODUCING ALCOHOL WITH A *PICHIA STIPITIS* STRAIN**

(71) Applicant: PROVINCE BRANDS, Toronto (CA)

(72) Inventor: Erin Johnson, London (CA)

(73) Assignee: Province Brands, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/521,102

(22) Filed: Jul. 24, 2019

(65) Prior Publication Data

US 2019/0345521 A1 Nov. 14, 2019

Related U.S. Application Data

(63) Continuation of application No. 12/914,236, filed on Oct. 28, 2010.

(60) Provisional application No. 61/272,744, filed on Oct. 18, 2009.

(51) Int. Cl.
*C12P 7/08* (2006.01)
*C12R 1/84* (2006.01)

(52) U.S. Cl.
CPC .................... *C12P 7/08* (2013.01); *C12R 1/84* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 4,701,414 A | 10/1987 | Van Dijken et al. | |
| 5,126,266 A | 6/1992 | Jeffries et al. | |
| 5,620,877 A | 4/1997 | Farone et al. | |
| 5,789,210 A | 8/1998 | Ho et al. | |
| 6,410,302 B1 | 6/2002 | Traff et al. | |
| 6,498,029 B2 | 12/2002 | Keller, Jr. et al. | |
| 7,226,735 B2 | 6/2007 | Jeffries et al. | |
| 7,253,001 B2 | 8/2007 | Wahlbom et al. | |
| 7,285,403 B2 | 10/2007 | Jeffries et al. | |
| 7,354,743 B2 | 4/2008 | Viasenko et al. | |
| 7,381,551 B2 | 6/2008 | Wahlbom et al. | |
| 7,527,927 B1 | 5/2009 | Ho et al. | |
| 7,531,348 B2 | 5/2009 | Cordero Otero et al. | |
| 2001/0036659 A1* | 11/2001 | Keller, Jr. | C12N 1/16 435/254.21 |
| 2009/0155872 A1 | 6/2009 | Abbas et al. | |

FOREIGN PATENT DOCUMENTS

| | | |
|---|---|---|
| WO | WO 84/04542 | 11/1984 |
| WO | WO 199400589 | 1/1994 |
| WO | WO1994000589 | * 1/1994 |

OTHER PUBLICATIONS

Slininger et al. Biotechnol Bioeng. Feb. 15, 2009;102(3):778-90. Published online Sep. 2, 2008 in Wiley InterScience (www.interscience.wiley.com) (Year: 2008).*
Rudolf et al. Biotechnol Bioeng. Mar. 1, 2008;99(4):783-90. Published online Sep. 4, 2007 in Wiley InterScience (www.interscience.wiley.com). (Year: 2007).*
Shi et al. Appl Microbiol Biotechnol. Sep. 1998;50(3):339-45. (Year: 1998).*
Slininger et al. Biotechnol Bioeng. Feb. 15, 2009; 102(3):778-90. Published online Sep. 2, 2008 in Wiley lnterScience ( www.interscience.wiley.com) (Year: 2008).
Rudolf et al. Biotechnol Bioeng. Mar. 1, 2008 ;99(4):783-90. Published online Sep. 4, 2007 in Wiley lnterScience ( www.interscience.wiley.com) (Year: 2007).
WO1994000589A1—Method for co-fermenting glucose and xylose into ethanol using a mixed microorganism culture—Google Patents English translation. Jan. 6, 1994. (Year: 1994).
Shi et al. Appl Microbial Biotechnol. Sep. 1998;50(3):339-45. (Year: 1998).
Esteve-Zarzoso, et al., Identification of yeasts by RFLP analysis of the 5.8S rRNA gene and the two ribosomal internal transcribed spacers. Int J Syst Bacteriol 49 (1999), 329-337; DOI 10.1099/00207713-49-1-329.

* cited by examiner

*Primary Examiner* — Christian L Fronda
(74) *Attorney, Agent, or Firm* — Ballard Spahr LLP (57) ABSTRACT

A novel isolated *Pichia stipitis* strain is provided. The strain is capable of fermenting at least a pentose sugar in the presence of one or more inhibitory substances to produce ethanol. A method of utilizing the strain to produce ethanol is also provided.

11 Claims, 6 Drawing Sheets

Figure 3: Fermentation with Minimal Medium (no yeast extract or peptone)

METHOD OF PRODUCING ALCOHOL WITH A *PICHIA STIPITIS* STRAIN

CROSS-REFERENCE TO RELATED APPLICATION

This application claims the benefit of U.S. Provisional Patent Application No. 61/272,744, filed Oct. 28, 2009, and incorporates such provisional patent application in its entirety by reference.

FIELD OF THE INVENTION

The present invention generally relates to industrially useful microorganisms, and in particular, relates to novel ethanol-producing yeast.

BACKGROUND OF THE INVENTION

The Renewable Fuels industry is facing increased pressure to expand production, employ a variety of feedstocks particularly those that are available in abundance but may be less desirable or more challenging in use, and to reduce costs. Within the bioethanol industry, there are two main sectors, classified by feedstock, namely: 1) starch and 2) lignocellulosic (biomass). There are approximately 168 operating starch-based ethanol facilities in North America that produced approximately 8 billion gallons of ethanol in 2008. There are approximately 11 biomass-based ethanol plants in the planning stages, with 1 commercial facility currently in operation.

Until recently, the feedstock used for the production of industrial alcohol by fermentation has been sugars from starch (rice, corn, sorghum, etc.), beets, sugar cane or other crops that potentially compete for food. It is believed that these crops will be too expensive in the future to be used as feedstock for the large-scale production of fuel ethanol. The most attractive renewable source of carbohydrates is plant biomass which can be grown in high density, grown on less attractive agricultural land and maintain stable costs. The major fermentable sugars from lignocellulosic materials include glucose, which accounts for about 30-50% of fermentable sugars, and xylose, which accounts for about 10-40% of the fermentable sugars. The most efficient fermentation of lignocellulosic materials would convert both glucose and xylose to ethanol. Unfortunately, to date, microorganisms capable of fermenting both glucose and xylose effectively and efficiently at industrial scale have not been identified.

*Saccharomyces* yeasts have been used for fermenting glucose-based feedstocks to ethanol and they are considered to be the best microorganisms for that industrial purpose due to their hardiness and tolerance to ethanol, organic acids and adverse environmental conditions. Unfortunately, *Saccharomyces* yeasts do not metabolize 5-carbon (pentose) sugars, rendering them inefficient for use to ferment plant biomass which comprises significant 5-carbon sugar (e.g. xylose) content. In the last two decades there has been much research into the genetic engineering of yeast and bacteria in order to develop a xylose-fermenting microorganism. However, wild-type and recombinant microorganisms that have been identified as having xylose-metabolizing activity exhibit ineffective xylose production, e.g. either too slow, incomplete, produce too many byproducts or unable to ferment under anaerobic conditions.

The development of recombinant microorganisms to metabolize xylose is hindered by the fact that metabolic pathways involved in xylose metabolism and their regulation, particularly in yeast, are still poorly understood. Although, genetic engineering technology can supply functional xylose metabolizing pathways in yeast that do not normally have this capacity, the regulatory network for xylose fermentation may still not be adequate. Many research facilities are involved in recombinant xylose-metabolizing yeast research yet there is not one successful strain for commercial application to lignocellulosic hydrolysates. Furthermore, there is a lack of knowledge with respect to how recombinant yeast will respond to wood hydrolysate, different feed strategies, oxygenation, inhibitory compounds, etc.

The only commercial demonstration plant producing ethanol from biomass (lignocellulosic material) has reported that they employ a recombinant *Saccharomyces* strain which was produced by the integration of the genes for xylose reductase (XR) and xylitol dehydrogenase (XDH) from *Pichia* sp and the *Saccharomyces xylulokinase* (XK) gene into a polyploid brewing host strain. The resulting strain exhibits conversion of glucose to ethanol, however, the extent, rate and efficiency of xylose conversion to ethanol by this strain is not confirmed.

In view of the foregoing, it is clear that a need exists for a microorganism that can efficiently ferment, e.g. a lignocellulose-based feedstock, to produce ethanol under industrially acceptable conditions.

SUMMARY OF THE INVENTION

Naturally occurring yeast of the species, *Pichia stipitis*, have now been identified which are capable of producing ethanol from pentose sugars in the presence of inhibitory substances under conditions suitable for industrial fermentation including anaerobic conditions.

Thus, in one aspect of the invention, an isolated *Pichia stipitis* strain is provided which is capable of fermenting pentose sugars in the presence of one or more inhibitory substances to produce ethanol under conditions in which the respiratory quotient is greater than 10.

In another aspect of the invention, a method of producing ethanol is provided comprising the step of incubating a *Pichia stipitis* strain as defined in a medium comprising at least a pentose sugar in the presence of at least one inhibitory substance under conditions in which the respiratory quotient is greater than 10.

These and other aspects of the invention will become apparent by reference to the detailed description that follows and the appended figures.

DETAILED DESCRIPTION OF THE INVENTION

Novel yeast of the species, *Pichia stipitis*, are provided, which are capable of fermenting pentose sugars in the presence of one or more inhibitory substances under anaerobic conditions to produce ethanol.

The present *Pichia stipitis* yeast can utilize pentose sugars such as xylose, and arabinose, as well as hexose sugars such as glucose, fructose, mannose and galactose; disaccharides such as sucrose, lactose, maltose and cellobiose; oligosaccharides such as maltotriose; and combinations of pentose and hexose sugars, in particular, xylose and glucose, to form ethanol. In the case of combined pentose and hexose feedstocks, pentose and hexose sugars are both utilized. It is noted that the present yeast does not respire ethanol in the presence of xylose, even in the presence of oxygen. The flexibility in utilizable feedstock renders the present *P. stipitis* strains particularly suitable to ferment feedstocks comprising both hexoses and pentoses including plant biomass comprising cellulose and hemicelluloses such as hydrolysates of lignocellulosic biomass. The term "lignocellulosic biomass" refers to plant biomass comprising cellulose and hemicelluloses that are tightly bound by the lignin. Lignocellulosic biomass includes wood residues (including sawmill and paper mill discards), municipal paper waste, agricultural residues (including corn stover and sugarcane bagasse), and dedicated energy crops.

Ethanol-producing fermentation by the present *P. stipitis* strains may be conducted aerobically or anaerobically. As one of skill in the art will appreciate, the term "fermentation" refers to the cultivation of yeast in which sugar is converted to alcohol and is independent of aeration regime. The term "anaerobic" as used herein refers to fermentation under conditions in which the respiratory quotient (RQ) is 50 or greater. Respiratory quotient is the ratio of the molar volumetric carbon dioxide production rate to the molar volumetric oxygen consumption rate. Anaerobic fermentation may be achieved with an influx of approximately 0.005 volume air to 1 volume total liquid per minute (vvm) or less. The term "aerobic" as used herein refers to fermentation under conditions in which the respiratory quotient is less than 50. Included within the meaning of aerobic, thus, is "microaeration" in which fermentation occurs when the respiratory quotient is greater than 10 and less than 50. In the microaerated condition, the culture vessel may be open to the atmosphere for the passive exchange of oxygen in air which is free to flow in the airspace over the top of the liquid in the vessel and which reaches an equilibrium with the oxygen concentration in the liquid. In this context, the exchange of oxygen in the microaerated environment is approximately equivalent to aerating a bioreactor at a rate of between about 0.05 to 0.005 volume air to 1 volume total liquid per minute (vvm). Strict aerobic conditions, thus, occur when the respiratory quotient (RQ) is less than 10, e.g. RQ may equal 1.

In addition, the present fermentation may be conducted in the presence of one or more inhibitory substances, such as those typically found in lignocellulosic hydrolysates, including furan derivatives, such as 2-furaldehyde (furfural), 5-hydroxymethyl-2-furaldehyde (HMF), 2-acetylfuran, 2,3-dihydro-5-methylfuran-2-one and levoglucosenome; aliphatic/carboxylic acids such as acetic, formic, glycolic, lactic and levulinic acids; and phenolic compounds such as phenol, guaiacol, vanillin, vanillic acid, cinnamaldehyde and ferulic acid.

The present yeast strain is able to ferment pentose and hexose sugars in minimal media, e.g. media void of vitamins (e.g. thiamine, riboflavin, niacin, B6, folic acid, biotin, CA-pantothenate), amino acids and peptides. Thus, the fermentation medium may be void of yeast extract and peptone, when supplemented with a source of nitrogen and minerals.

The ethanol yield of the present *P. stipitis* strains has been determined to be at least about 0.30 grams of ethanol per gram of xylose, preferably at least about 0.39 grams per gram of xylose, under anaerobic conditions, in the presence of inhibitory substances typically present in lignocellulose hydrolysates, in minimal media (no vitamins), with minimal by-product formation (e.g. less than 0.05 g xylitol and less than 0.005 g glycerol per gram of xylose).

Furthermore, the present yeast strains exhibit high rates of pentose/hexose uptake of at least about 2.0 g/L per hour, and preferably uptake rates of at least about 4.0 g/L per hour, and more preferably a pentose/hexose uptake rate of at least about 5.0 g/L per hour. As one of skill in the art will appreciate, pentose/hexose uptake rate varies with a number of factors including cell concentration and level of aeration. Thus, the greater the aeration, e.g. anaerobic versus microaerobic conditions, the greater the sugar uptake, and the greater the yeast cell concentration, the greater the sugar uptake. For example, under microaerobic conditions, the present yeast strain exhibits a xylose uptake rate of at least about 3.5 g/L per hour and up to about 8-9 g/L per hour as compared to the uptake rate under anaerobic conditions with a similar yeast cell concentration.

*Pichia stipitis* strains in accordance with the present invention may be isolated from appropriate natural environments, for example from natural samples rich in hemicellulose and cellulose such as silage, wet composting hay, horse manure and sheep manure, using selective culturing techniques well-established in the art that are suitable to isolate yeast capable of utilizing a pentose sugar such as xylose or arabinose as a carbohydrate source. The properties of selected colonies may then be determined, e.g. rate of xylose uptake, rate/yield of ethanol production, by-product formation, ability to grow in the presence of selected inhibitory substances and ability to grow in minimal media (lacking vitamins). A *Pichia stipitis* strain in accordance with an embodiment of the invention, herein referred to as *P. stipitis* BTRUK2, was deposited at the International Depository Authority of Canada (IDAC) under deposit number 201009-01 on Oct. 20, 2009.

Thus, the *Pichia stipitis* strain of the present invention exhibits a number of properties which render it particularly useful for industrial scale fermentation of hydrolyzed plant biomass, including the ability to ferment both pentose and hexose sugars in the presence of inhibitory substances typical of such hydrolysates under anaerobic conditions and in minimal media, while exhibiting high rates of sugar uptake and ethanol production.

In another aspect of the present invention, a method of producing ethanol is provided comprising culturing a *Pichia stipitis* strain, such as *P. stipitis* BTRUK2, in a medium comprising at least pentose sugar and one or more inhibitory substances selected from the group consisting of furans, phenolic compounds and organic acids, under anaerobic or microaerobic conditions as previously described. The medium may additionally comprise a hexose sugar, such as glucose, fructose, galactose or mannose; a dissaccharide such as sucrose, maltose, lactose or cellobiose; or an oligosaccharide such as maltotriose. In the presence of pentose and hexose sugars, each are utilized. In addition, a minimal medium may be employed that lacks nutrients such as vitamins, minerals, amino acids and peptides.

This fermentation method is conducted under conditions suitable for the yeast to produce ethanol, including a temperature in the range of about 20°-40° C., preferably a temperature in the range of 25°-35° C., and more preferably a temperature of about of 25°-30° C., and a pH in the range of about 4.0 to 8.0, preferably about 4.5-7.5, and more preferably a pH in the range of about 5.0-7.5.

According to the present method, sugar uptake is at least about 2 g/L per hour under anaerobic conditions and up to about 8-9 g/L·hr microaerobically. Ethanol yields utilizing the present method under anaerobic conditions are at least about 0.30 grams per gram of sugar, while ethanol yields of at least about 0.40 grams per gram of sugar, and preferably at least about 0.45 grams per gram of sugar, are attained under microaerobic conditions.

As will be apparent to one of skill in the art, the present method encompasses a method of producing ethanol from hydrolysates of lignocellulosic biomass.

Embodiments of the invention are described in the following examples which are not to be construed as limiting.

Example 1—Isolation of a Xylose-Fermenting *Pichia* Strain

The following were employed in the isolation of the xylose-fermenting *Pichia* strain: Yeast Nitrogen Base (YNB) which contains salts, vitamins and trace elements as follows: potassium phosphate (1000 mg/L), inositol (2 mg/L), copper sulfate (0.04 mg/L), magnesium sulfate (500 mg/L), niacin (0.4 mg/L), potassium iodide (0.1 mg/L), sodium chloride (100 mg/L), PAA (0.2 mg/L), ferric chloride (0.2 mg/L), calcium chloride (100 mg/L), pyridoxine (0.4 mg/L), manganese sulfate (0.4 mg/L), biotin (0.002 mg/L), riboflavin (0.2 mg/L), sodium molybdate (0.2 mg/L), pantothenate, calcium (0.4 mg/L), thiamine (0.4 mg/L), zinc sulfate (0.4 mg/L), folic acid (0.002 mg/L), boric acid (0.5 mg/L); YNB without amino acids (YNB w/o AA) which contains ammonium sulphate as a nitrogen source and is used in preparing carbohydrate selective media; and YNB without amino acids and without ammonium sulphate (YNB w/o AA, w/o AS) which contains no carbohydrate or nitrogen source and is used in preparing both a carbohydrate and a nitrogen selective media. Unless otherwise specified, cultivation temperature was 28° C. with 160 rpm mixing speed.

Samples from natural environments rich in hemicellulose and cellulose such as silage, hay compost, sheep and horse manure were cultured in selective liquid defined medium (YNB w/o AA w/o AS, 1.7 g/L; xylose, 5 g/L; L-lysine, 1 g/L) in order to select yeast that could grow on xylose as the sole carbohydrate source and lysine as the sole amino acid. The cultures were then filtered and plated onto solid agar selective medium (YNB w/o AA w/o AS, 1.7 g/L; xylose, 5 g/L; L-lysine, 1 g/L) using the plate count method and targeting 100-200 cell/plate. Yeast colonies were selected using colony morphology and microscopic examination. Individual yeast isolates that grew strongly on the xylose-lysine plates were further isolated and a strain strengthening procedure was performed.

Strain strengthening was performed on each single colony isolate by placing a small loop of the isolate into 10 ml of liquid defined medium (YNB w/o AA w/o AS, 1.7 g/L; xylose, 5 g/L; L-lysine, 1 g/L). After 48 hours, 100 µL of the seed culture was inoculated into 10 ml fresh liquid defined medium of the same composition. This was repeated twice more. After strain strengthening, cultures of single colony isolates were plated once more onto solid agar selective medium (YNB w/o AA w/o AS, 1.7 g/L; xylose, 5 g/L; L-lysine, 1 g/L) using cell count methods and concentrations of 100-200 cell/plate. All plates were wrapped with parafilm to eliminate cross feeding and this confirmed selection for xylose and lysine as sole carbohydrate and nitrogen sources, respectively.

Isolates were selected based on the fact that they showed strong growth on xylose-lysine plates and were further selected based on ethanol production in anaerobic environments utilizing xylose. This was accomplished by taking the positive single colony isolates from xylose-lysine plates, inoculating into 10 ml liquid defined medium (YNB w/o AA w/o AS, 1.7 g/L; xylose, 5 g/L; L-lysine, 1 g/L), cultivating in test tubes wrapped with parafilm to seal off the aerobic atmosphere and culturing the test tubes for 48 hours at 28° C. with mixing at 160 rpm. Isolates that were able to utilize xylose anaerobically and produce ethanol were identified as those tubes with growth, foam, swollen parafilm and an alcoholic smell upon release of the parafilm.

The successful test tubes (single isolates) were centrifuged (3,000 rpm, 5 minutes, 4° C.), washed three times with sterile water and streaked onto solid agar selective medium (YNB w/o AA w/o AS, 1.7 g/L; xylose, 5 g/L; L-lysine, 1 g/L) for storage at 4° C.

In order to confirm and quantify the anaerobic production of ethanol from xylose, each isolate was cultured in liquid defined medium (YNB w/o AA w/o AS, 1.7 g/L; xylose, 5 g/L; L-lysine, 1 g/L) by placing one loopful of yeast into 10 ml of medium and culturing at 28° C. for 24 hours. Ethanol and xylitol yields and production and xylose consumption was determined using HPLC analysis. The isolates with low xylitol and high ethanol production in combination with high xylose uptake were chosen to proceed to the next stage.

The characteristics of a selected isolate were determined by plating on selective plates for: tolerance to cycloheximide 4 mg/L; melibiose as sole carbohydrate; maltose as sole carbohydrate; tolerance to lactic acid concentration of 5.6 g/L. The isolate was also tested for growth at 37° C. and 40° C. using xylose-lysine YNB solid medium.

Growth characteristics of the selected xylose-fermenting yeast, which formed round, soft whitish colonies, are set out in Table 1.

TABLE 1

| Parameter | Growth |
| --- | --- |
| 37° C. | weak |
| 40° C. | negative |
| 4 mg/L cycloheximide | positive |
| Xylose | positive |
| lysine as sole amino acid | positive |
| melibiose/YNB | negative |
| maltose/YNB | positive |
| lactic acid (5.61 g/L lactic acid/YEPG) | positive |
| 5.61 g/L lactic acid/xylos/lysine/YNB | positive |

Further fermentation testing was performed to evaluate yeast performance. A summary of its characteristics were as follows:

1. Simultaneous utilization of glucose and xylose up to glucose concentration of 20 g/L.
2. Fermentation of xylose to ethanol under anaerobic conditions at yields as high as 0.39 g ethanol/g xylose. In this context, anaerobic conditions refer to the conditions which create an RQ of 50 or higher, achieved generally with an influx of approximately 0.005 volume air to volume total liquid per minute (vvm) or less in a flask stoppered so that it is air tight. A 16 gauge needle was pushed through the stopper to vent the pressure created by the production of carbon dioxide.

3. Fermentation of xylose to ethanol in microaerobic conditions at yields of at least 0.44 g ethanol/g xylose including at 0.50 g ethanol/g xylose. Microaerobic conditions refer to the condition which create an RQ between 10 and 50, achieved generally with an influx of approximately 0.05 volume air to volume total liquid per minute (vvm) or simulated in a flask fermentation by not sealing the vessel and allowing air to passively flow over the liquid surface.

4. Fermentation of glucose and xylose in the presence of inhibitory compounds found in lignocellulosic hydrolysates such as phenols, organic acids and furan derivatives with yields of ethanol of >0.45 g ethanol/g xylose, e.g. 0.49 g ethanol/g xylose under micro-aerobic conditions.

5. Metabolizes xylose at a rate as high as 8.7 g/L·hr depending on cell concentration and aeration (For microaerobic conditions, a cell concentration of 6.7 g/L d.b. resulted in a xylose uptake of 3.45 g/L·hr and a cell concentration of 28.5 g/L d.b. resulted in a xylose uptake rate of 8.7 g/L·hr).

6. Ferments glucose and xylose to ethanol in the absence of any vitamin supplementation at yields greater than 0.47 g ethanol/g xylose in microaerobic environments and 0.39 g ethanol/g xylose in anaerobic environments.

7. Cell growth rates remain positive for very high ethanol concentrations, e.g. ethanol concentrations reaching at least about 130 g/L.

8. Ethanol produced in aerobic or anaerobic fermentations is not respired or consumed by the yeast until both glucose and xylose are exhausted from the medium. Ethanol will continue to be produced and will not be respired even if glucose has been exhausted if xylose is still present in the medium. Xylose is therefore considered to be a 'fermentable' sugar by this yeast.

9. Cells grow on xylose even in the absence of air (e.g. under anaerobic conditions).

11. The yeast exhibited very low yield of by-products under aerobic or anaerobic fermentation of xylose including xylitol (<0.05 g/g) and glycerol (<0.006 g/g).

12. The yeast has a very low yield of by-products under aerobic or anaerobic fermentation of glucose including glycerol (<0.009 g/g).

13. Fermentation tests were performed to confirm that the *Pichia stipitis* yeast strain could metabolize other sugars in a microaerobic environment. Nine sugars were tested (galactose, maltodextrin, lactose, mannose, fructose, xylitol, arabinose, cellobiose and maltotriose). All sugars were added to liquid medium at 10 g/L with YNB w/o AAs, 6.7 g/L. Fermentations were incubated at 28° C. and 160 rpm with an initial cell concentration of 5 g/L d.b. Fermentations were 48 hours long and HPLC analysis was performed to evaluate the utilization of the sugars (samples at time zero and 48 hours). All sugars listed were utilized by this *Pichia stipitis* yeast strain with the exception of the DP(4) and DP(5+) portion of the maltodextrin. The maltodextrin was 0.3% of DP(1), 0.9% of DP(2), 1.4% DP(3), 1.4% DP(4), and 96.0% is DP(5+), where DP stands for "Degree of Polymerization, and refers to the number of glucose monomers.

The general experimental procedure applied aerobic propagation of yeast cells in a liquid medium (10 g/L glucose, 50 g/L xylose, 10 g/L yeast extract and 20 g/L peptone) harvesting the cells in exponential growth phase by centrifugation, washing once with sterile water and resuspending them in fresh medium resulting in a final fermentation mixture containing (approx.) 5-28 g (dry weight) cells/L as specified.

Concentrations of glucose, maltose, DP3, DP4, glycerol, ethanol, acetic acid, lactic acid, glycerol, HMF, furfural, formic acid were determined by off-line analysis on an HP 1050 HPLC system. The HPLC consisted of an Agilent 1050 isocratic pump, autosampler and column compartment and a 1047A RI detector. The method parameters were: a pump run time of 25 minutes; a pump flow rate of 0.6 ml/min; a mobile phase of 5.0 mM $H_2SO_4$; a column temperature of 65° C., a detector temperature of 35° C., an injection volume of 10 μL; RIU/FS of 1/8. The column used was the Biorad Aminex HPX-87H (Bio-Rad Laboratories). The samples were first filtered through 1.6 μm glass fiber, and diluted to the appropriate levels then filtered through 0.22 μm nylon syringe filter.

Biomass dry weight was determined gravimetrically from duplicate 5 ml aliquots. Each 5 ml aliquot of sample was filtered through a glass fiber filter paper (Fisherbrand G6, 1.6 microns), washed with 50 ml ultrafilterd (Milli-Q) water and dried in the oven at 105° C. The filter paper and aluminum dish were pre-weighed before filtration and again after the drying step. This results in a mass/volume (g/L) measure directly. The biomass dry weight. is therefore a measure of total undissolved solids. Cell biomass (g/L dry wt) is obtained by subtracting the measure of a 'blank' sample (solids without cell biomass) from the fermentor sample (cell plus 'other' solids). Of interest is the change in biomass and thus cell yields over time. Cell growth (expressed as g/L, D.W.) was measured using gravimetric techniques Example 2: The Effect of pH A pH Study was performed to determine optimal operating pH of glucose/xylose fermentation using the yeast of Example 1. The medium contained glucose (10 g/L) and xylose (50 g/L). Both anaerobic and slightly aerobic conditions were tested. A pH of 5.5 resulted in the highest yield of ethanol from xylose (0.5 g/g) in the passively aerated tests. For strict anaerobic studies, pH of 6.4 resulted in the highest yield of ethanol from glucose and xylose.

The operating parameters were as follows: temperature was 30° C., pH varied (4.5, 5.5, 6.4), initial cell concentration was 9-9.5 g/L d.b., batch fermentation (100 ml). The medium was pure sugars with yeast extract and peptone.

Figure 1:
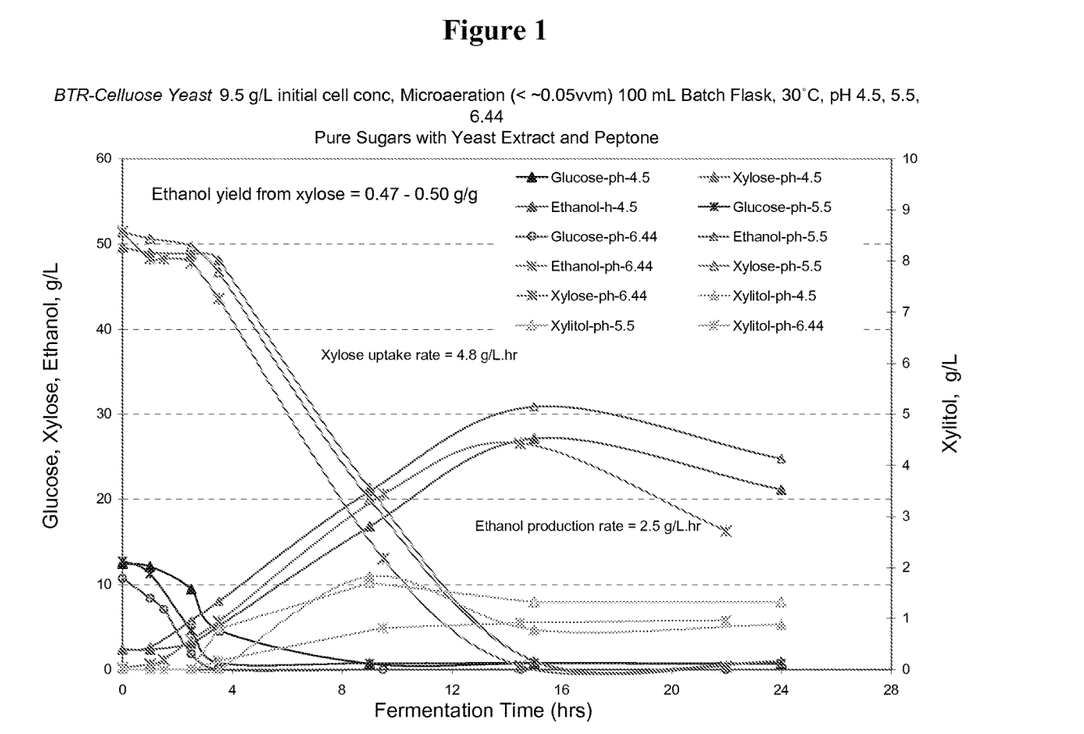
FIG. 1 graphically illustrates the results of xylose and glucose fermentation with varied pH using a *Pichia stipitis* strain according to an embodiment of the invention.

Results for microaeration (<0.05 vvm) were obtained from the rubber-stoppered batch container through a hole in hole in the rubber stopper that was covered with foil. The batch was sampled at times: 0, 1, 2.5, 3.5, 9, 15 and 24 hrs. High uptake rates of xylose (4.8-5.0 g/L·hr) and high production rates of ethanol (2.5 g/L·hr) were observed. Ethanol yield from xylose was 0.47-0.50 g/g. Xylose was consumed by 14-15 hrs (50 g/L). Low yield of glycerol (0.002-0.006 g glycerol/g glucose & xylose) was observed. Xylitol production and yield were very low (<0.02 g xylitol/g xylose). These results are illustrated in FIG. 1.

Example 3: The Effect of Temperature

A temperature study was performed to determine optimal operating temperature of glucose/xylose fermentation using the yeast of Example 1. The medium contained glucose (10 g/L) and xylose (50 g/L). Both anaerobic and passive aerobic conditions were tested. A temperature of 25° C.

resulted in the most rapid fermentation, although fermentation at 35° C. was viable. For the aerobic study, yields of ethanol from glucose and xylose reached 0.49 g/g. For strict anaerobic studies, the ethanol yield from glucose and xylose was slightly higher at 25° C. as compared to 35° C.; however, xylose was used quicker in the latter.

The operating parameters used in the study were as follows: temperature of 25° C. and 35° C., pH of 5.5, initial cell concentration of 8 g/L d.b. and batch flask fermentation (100 ml). The medium was pure sugars with yeast extract and peptone.

Figure 2:
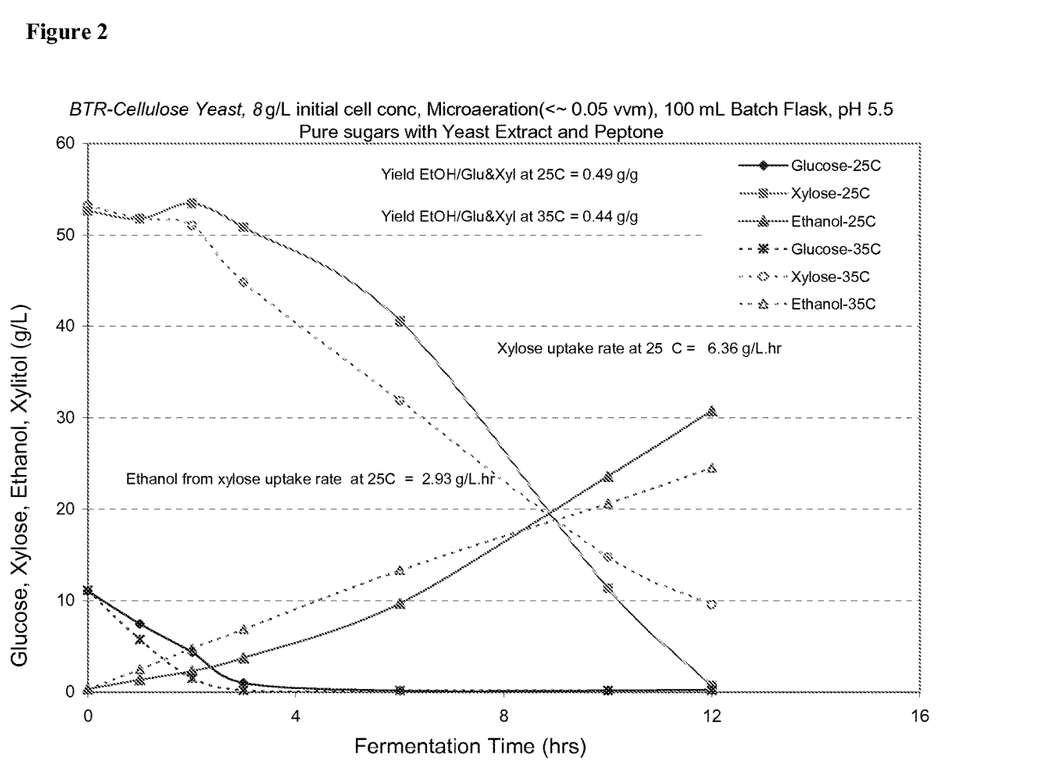
FIG. 2 graphically illustrates the results of xylose and glucose fermentation with temperature variation using a *Pichia stipitis* strain.

The results for the microaeration (<0.05 vvm) fermentation were obtained as described above at 0, 1, 2, 3, 6 and 12 hrs. Uptake rates for xylose were determined to be about 6.4 g/L·hr with production rates of ethanol of 2.9 g/L·hr. Ethanol yield from xylose was 0.50 g/g and ethanol yield from glucose and xylose was 0.49 g/g at 25° C., and 0.44 g/g at 35° C. A low yield of glycerol (0.004-0.008 g glycerol/g glucose & xylose) was observed, as well as low production and yields of xylitol. Xylose was consumed within 12 hrs at 25° C. These results are illustrated in FIG. 2.

Example 4: The Effect on Fermentation of Media Lacking Vitamins

For this study macro and micro nutrients were selected that are feasibly available for industrial scale production. Yeast extract and peptone were not added. Thus, the activity of the yeast of Example 1 on pure sugars with a minimal medium was determined. The macro and micro nutrients supplemented were as follows:

Macro Nutrients

| | |
|---|---|
| $(NH_4)_2SO_4$ | 6.6 g/L |
| $KH_2PO_4$ | 3.5 g/L |
| $MgSO_4 \cdot 7H_2O$ | 1.0 g/L |
| $CaCl_2$ | 0.40 g/L |

Micro Nutrients (Trace Supplements)

| | |
|---|---|
| $CaCl_2 \cdot 2H_2O$ | 860 mg/L |
| $Fe(SO_4) \cdot 7H_2O$ | 400 mg/L |
| $H_3BO_3$ | 200 mg/L |
| $CuSO_4 \cdot 5H_2O$ | 60 mg/L |
| KI | 20 mg/L |
| $ZnSO_4 \cdot 7H_2O$ | 600 mg/L |
| $MnCl_2$ | 150 mg/L |

The amount of glucose in the medium was increased to 40 g/L with xylose at 40 g/L in order to test the preferential selectivity of sugars. The yeast showed simultaneous utilization of glucose and xylose. In addition, the results showed steady ethanol production and high yields from xylose. There was no respiration of ethanol as long as xylose was present and thus xylose sugar appeared to be a 'fermentative' sugar. The yeast was able to maintain standard anaerobic growth rates under these supplemental conditions (0.083 g cell/g sugar, d.b.).

Figure 3:
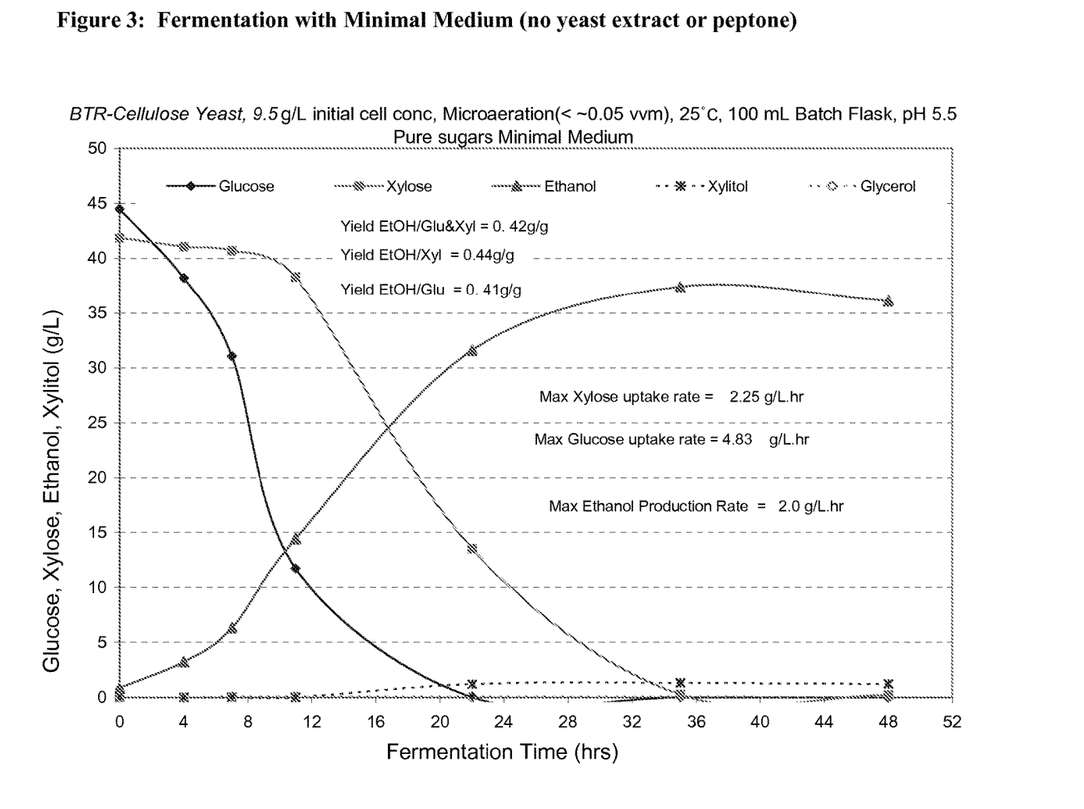
FIG. 3 graphically illustrates the results of combined xylose/glucose fermentation in minimal medium using a *Pichia stipitis* strain.

The results for the microaeration (<0.05 vvm) fermentation were obtained as described above at 0, 4, 7, 11, 22, 35 and 48 hrs. Maximum uptake rates for xylose were determined to be about 2.25 g/L·hr with maximum production rates of ethanol of 2.0 g/L·hr. Ethanol yield from xylose was 0.44 g/g at 25° C. No significant amount of glycerol was observed, as well as low production and yield of xylitol (0.03 g/g). These results are illustrated in FIG. 3.

Example 5: The Effect of Stress Factors

In this study, the yeast of Example 1 was fermented using pure sugar medium with minimal nutrients and a stress factor at 25° C. and 160 rpm. The nutrient supplement was the same as described in Example 4 and was also void of yeast extract and peptone. A stress factor supplement was added to mimic a biomass hydrolysate. The amount of glucose in the medium was 40 g/L and the amount of xylose was 40 g/L in order to test the preferential selectivity of sugars. The following stress factor supplement was included in the fermentation.

Stress Factors were as follows:

| | |
|---|---|
| Lactic Acid | 0.6 g/L |
| Formic Acid | 1.4 g/L |
| Acetic Acid | 4.0 g/L |
| Levulinic Acid | 2.0 g/L |
| HMF | 1.0 g/L |
| Furfural | 3.0 g/L |

Surprisingly, yeast growth in this highly stressed mainly anaerobic environment was 0.084 g cell/g sugar (d.b.). There was simultaneous utilization of glucose and xylose. There was consistent fermentation performance compared to that shown in Example 4, although at a slower rate. There was no respiration of ethanol after glucose was exhausted.

Figure 4:
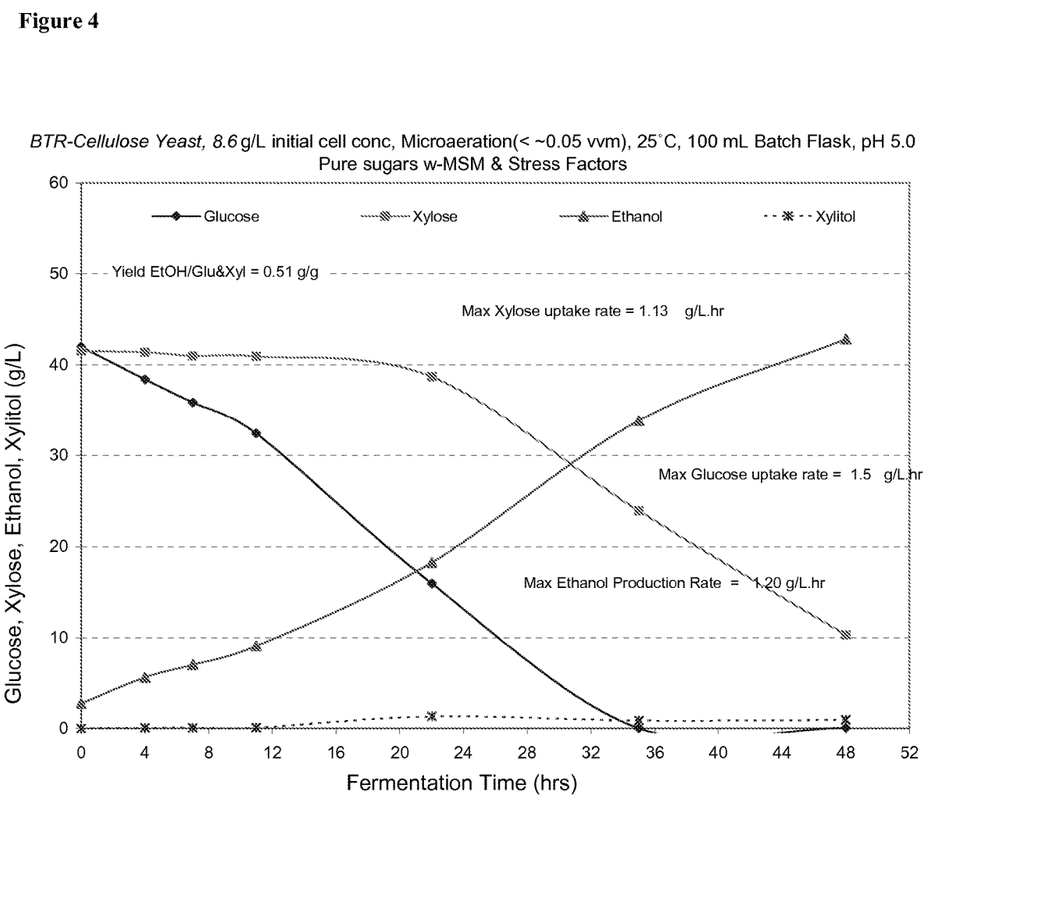
FIG. 4 graphically illustrates the results of combined xylose/glucose fermentation in a stressed environment (inhibitory substances and minimal medium) using a *Pichia stipitis* strain.

The results for the microaeration (<0.05 vvm) fermentation were obtained as described above at 0, 4, 7, 11, 22, 35 and 48 hrs. Maximum uptake rates for xylose were determined to be about 1.13 g/L·hr with maximum production rates of ethanol of 1.12 g/L·hr and a maximum uptake rate of glucose of 1.5 g/L·hr. Ethanol yield from glucose and xylose was 0.51 g/g at 25° C. A low production and yield of xylitol (0.03 g/g) resulted. These results are illustrated in FIG. 4.

This stress factor supplement would not normally be encountered in industry. In fact, a concentration of 4 g/L acetic acid would inhibit growth and ethanol production in most yeast. Thus, these results clearly illustrate the capability of this yeast.

Example 6—DNA Analysis

Polymerized Chain Reaction—Internal Transcribe Sequences (PCR-ITS) is a method which allows the identification of the genus and species of yeast. The amplification of a specific sequence of the ribosomal DNA will generate a fragment of variable size depending on the genus/species of yeast analyzed. If the size of a fragment is identical between two species, a digestion of the fragments is performed using restriction enzymes. The digestion will generate fragments cut at different places according to the species being analyzed and the digestion enzyme. The size of the fragments (digested and non-digested) can be compared to a database comprising 200 species of yeast.

PCR (ITS) with primers ITS1 and ITS4 were used followed by DNA digestion by Cfo-I, Hae-III and Hinf-1. This was performed by Siebel Institute of Technology, Lallemand, Royalmount, Montreal, Qc, Canada. With no restriction enzymes the fragment was 650 base pairs (bp). With CfoI there were two fragments one 300 bp and one 285 bp. With HaeIII there were two fragments, one was 490 bp and one was 140 bp. With HinfI there was one fragment that was 310 bp. The results were compared to tables of identification available in the literature (Esteve-Zarzoso et al., Inst. J. Syst. Bacteriol. 49: 329-337, 1999). The species was identified as *Pichia stipitis*.

For confirmation of genus and species sequencing of the domain D1-D2 of the 26s ribosomal DNA was conducted by Siebel Institute of Technology, Lallemand. The results were analyzed using "Blast" database and the yeast was confirmed to be *Pichia stipitis*.

Example 7—Effect of Cell Concentration on Xylose Uptake and EtOH Production Rate The effect of yeast cell concentration on xylose uptake and ethanol production rates was determined. Different concentrations of yeast cells (e.g. 6.7, 14.2 and 28.5 g/L d.b.) were incubated at 160 rpm at a temperature of 28° C. The cells were incubated in a medium including glucose (10 g/L), xylose (45 g/L), yeast extract (10 g/L) and peptone (20 g/L), pH 6.2, under conditions of microaeration (<0.05 vvm). Tin foil covered the flask opening.

It was found that the initial yeast cell concentration had a significant effect on the xylose uptake and ethanol production rate as set out in the Table 2 below.

TABLE 2

| Initial Cell conc'n (g/L) | Xylose uptake (g/L · hr) | Ethanol Production (g/L · hr) | Ethanol Yield (g/g xylose) |
|---|---|---|---|
| 6.7 | 3.45 | 2.01 | 0.51 |
| 14.2 | 6.36 | 3.25 | 0.49 |
| 28.5 | 8.66 | 4.01 | 0.46 |

Figure 5:
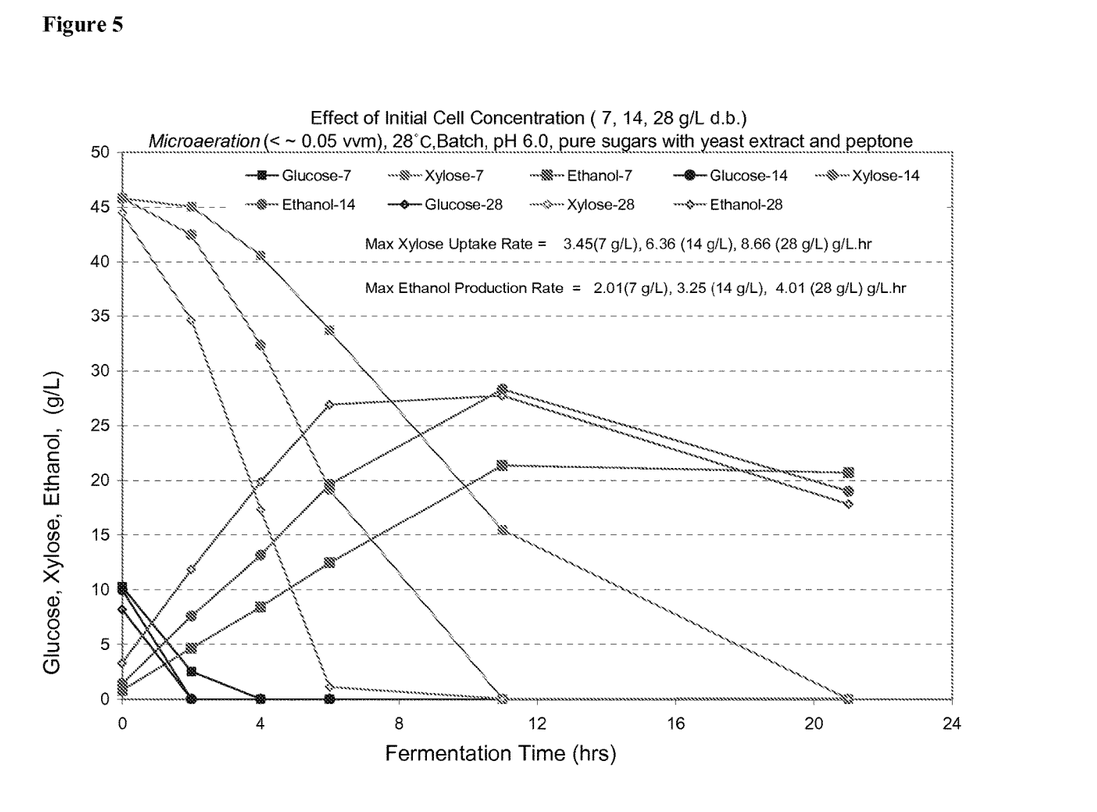
FIG. 5 graphically illustrates the results of anaerobic metabolism of xylose using a *Pichia stipitis* strain.

The results for the microaeration (<0.05 vvm) fermentation were obtained as described above at 0, 2, 4, 6, 11 and 24 hrs. Ethanol yield from glucose and xylose was 0.51 g/g at 25° C. with 6.7 g/L d.b. initial cell concentration. These results are illustrated in FIG. 5. As the initial cell concentration increased, the glucose and xylose uptake rates increased as did the ethanol production rate but the ethanol yield was slightly reduced. This indicates that the higher initial cell concentration, although resulting in increased fermentation times, requires more sugar energy for cell maintenance. The benefits of the increased fermentation time with increased initial cell concentrations will be advantageous at industrial scale and outweighs the smaller loss of yield. In increasing the initial cell concentration from 6.7 to 28.5 g/L d.b., fermentation time was reduced from about 17 hours to 6 hours.

Example 8—Anaerobic Xylose Uptake and EtOH Production Rate

The effect of anaerobic environment on xylose uptake and ethanol production rates was determined. The concentration of yeast cells was 8.8 to 9.7 g/L d.b. Flasks were incubated at 160 rpm at a temperature of 28° C. The cells were incubated in a medium including glucose (10 g/L), xylose (48 g/L), yeast extract (10 g/L) and peptone (20 g/L), pH 5.8, under anaerobic conditions (<0.005 vvm or an RQ>50). Flasks were stoppered and sealed air tight with a 16 gauge needle inserted through the rubber stopper.

Figure 6:
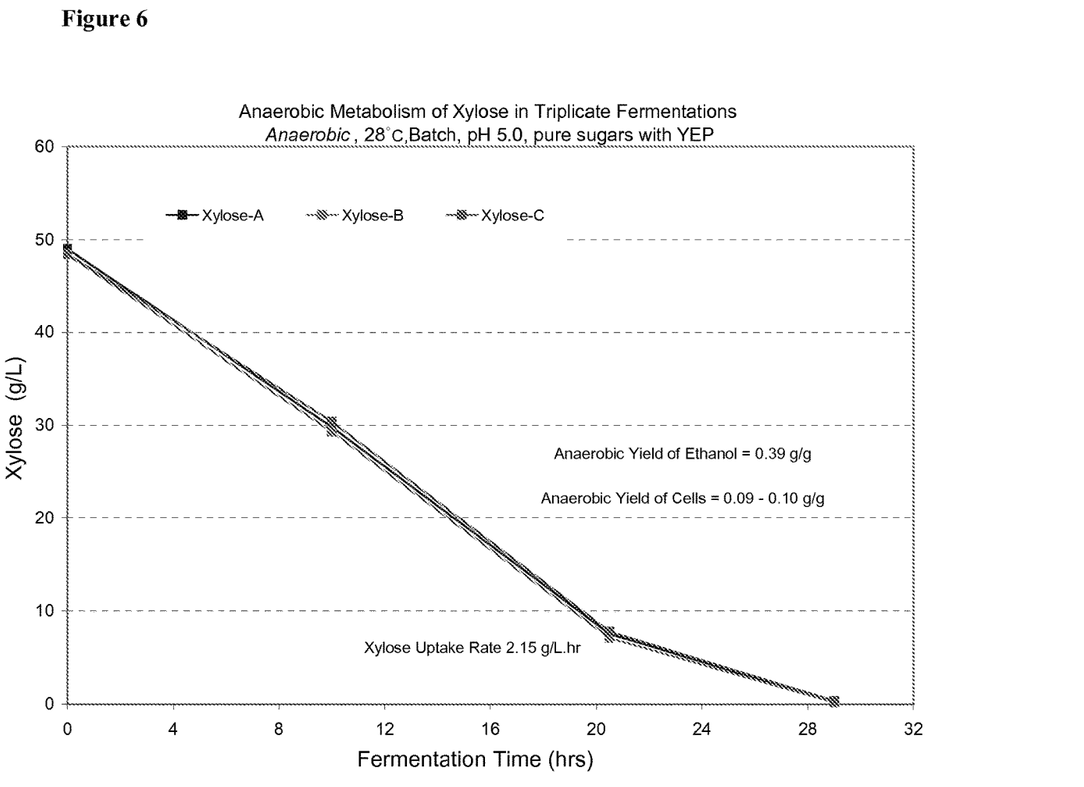
FIG. 6 graphically illustrates the results of the effect of altering the initial cell concentration on the uptake rate of xylose and the production rate of ethanol using a *Pichia stipitis* strain.

The results for the anaerobic fermentations in triplicate were obtained as described above at 0, 10, 20.5 and 29 hrs. Maximum uptake rates for xylose were determined to be about 2.15 g/L·hr with ethanol yield from glucose and xylose of 0.39 g/g at 28° C. A low production and yield of xylitol (0.03 g/g) resulted. These results are illustrated in FIG. 6.

I claim:

1. A method of producing alcohol comprising culturing a *Pichia stipitis* strain deposited under IDAC deposit number 201009-01 in a medium compromising at least a pentose sugar.

2. The method as defined in claim 1, wherein the medium includes a hexose sugar.

3. The method as defined in claim 2, wherein the medium comprises xylose and glucose.

4. The method as defined in claim 1, wherein the strain can produce ethanol in a medium that lacks vitamins.

5. The method as defined in claim 1, wherein the strain can produce ethanol in the presence of at least one inhibitory substance.

6. The method as defined in claim 5, wherein the inhibitory substance is selected from the group consisting of a furan derivative, an aliphatic carboxylic acid and a phenolic compound.

7. The method as defined in claim 1, wherein the RQ is at least about 10.

8. The method as defined in claim 1, wherein the pH is in the range of about 4.5-7.5 and the temperature is in the range of about 25°-40° C.

9. The method of claim 1, wherein a source of the xylose is a hemicellulose and cellulose material.

10. The method of claim 1, wherein the hemicellulose and cellulose material is selected from silage, hay compost, and manure.

11. A method of propagating a *Pichia stipitis* strain deposited under IDAC deposit number 201009-01 comprising culturing the *Pichia stipitis* strain deposited under IDAC deposit number 201009-01 in a medium comprising a pentose or a heptose sugar.

* * * * *